US009445613B2

(12) United States Patent
Harel

(10) Patent No.: US 9,445,613 B2
(45) Date of Patent: Sep. 20, 2016

(54) MICROENCAPSULATION OF BIOACTIVE SUBSTANCES AND METHODS OF MAKING THE SAME

(75) Inventor: Moti Harel, Pikesville, MD (US)

(73) Assignee: ADVANCED BIONUTRITION CORPORATION, Columbia, MD (US)

( * ) Notice: Subject to any disclaimer, the term of this patent is extended or adjusted under 35 U.S.C. 154(b) by 0 days.

(21) Appl. No.: 13/260,388

(22) PCT Filed: Mar. 24, 2010

(86) PCT No.: PCT/US2010/028432
§ 371 (c)(1),
(2), (4) Date: Nov. 11, 2011

(87) PCT Pub. No.: WO2010/111347
PCT Pub. Date: Sep. 30, 2010

(65) Prior Publication Data
US 2012/0058195 A1    Mar. 8, 2012

Related U.S. Application Data

(60) Provisional application No. 61/163,728, filed on Mar. 26, 2009.

(51) Int. Cl.
| | |
|---|---|
| *A61K 9/16* | (2006.01) |
| *A23L 1/00* | (2006.01) |
| *A21D 2/14* | (2006.01) |
| *A23L 1/03* | (2006.01) |
| *A23L 1/275* | (2006.01) |
| *A23L 1/30* | (2006.01) |
| *A23L 1/302* | (2006.01) |
| *A23L 1/304* | (2006.01) |
| *A23L 1/305* | (2006.01) |

(52) U.S. Cl.
CPC .............. *A23L 1/0032* (2013.01); *A21D 2/14* (2013.01); *A23L 1/034* (2013.01); *A23L 1/2753* (2013.01); *A23L 1/302* (2013.01); *A23L 1/304* (2013.01); *A23L 1/3008* (2013.01); *A23L 1/3051* (2013.01); *A23V 2002/00* (2013.01)

(58) Field of Classification Search
CPC .... A61K 9/50; A61K 9/5005; A61K 9/5057; A61K 9/5063; A61K 9/5073
USPC ................................................ 424/465–500
See application file for complete search history.

(56) References Cited

U.S. PATENT DOCUMENTS

| | | | |
|---|---|---|---|
| 4,350,679 A | | 9/1982 | Mizuno et al. |
| 4,765,996 A | * | 8/1988 | Misaki et al. .................. 426/72 |
| 4,871,558 A | * | 10/1989 | Tackikawa et al. ............ 426/99 |
| 5,258,132 A | | 11/1993 | Kamel et al. |
| 5,789,014 A | | 8/1998 | Maruyama et al. |
| 5,897,896 A | * | 4/1999 | Thomas ........................ 426/94 |
| 2005/0019416 A1 | | 1/2005 | Yan |
| 2005/0255202 A1 | * | 11/2005 | Dalziel ..................... A23F 5/14 426/302 |
| 2006/0051425 A1 | | 3/2006 | Kvitnitsky et al. |
| 2006/0067984 A1 | * | 3/2006 | Cavassini ............. A23K 1/003 424/438 |
| 2007/0042184 A1 | | 2/2007 | Coyne et al. |
| 2007/0098853 A1 | * | 5/2007 | van Lengerich ...... A21D 2/165 426/99 |

FOREIGN PATENT DOCUMENTS

| | | |
|---|---|---|
| CN | 1181216(A) | 5/1998 |
| EP | 0380066 A1 | 8/1990 |
| EP | 0824000 A1 | 2/1998 |
| EP | 1 649 763 A1 | 4/2006 |
| JP | S63-173568 A | 7/1988 |
| JP | H02-276551 A | 11/1990 |
| JP | S64-003118 A | 1/1996 |
| JP | H10-203965 A | 8/1998 |
| JP | 2000-026283 | 1/2000 |
| KR | 10-2007-0014685 | 2/2007 |
| KR | 10-0708810 | 4/2007 |
| WO | WO 2004/082660 A1 | 9/2004 |
| WO | WO 2005067894 | 7/2005 |
| WO | 2006-522739 A | 10/2006 |
| WO | WO 2008/017962 A2 | 2/2008 |
| WO | WO 2008017962 A2 * | 2/2008 |

OTHER PUBLICATIONS

Gelatin (http://en.wikipedia.org/wiki/Gelatin) downloaded May 15, 2015.*
Beeswax (http://en.wikipedia.org/wiki/beeswax) downloaded May 15, 2015.*
International Search Report for International Application No. PCT/US2010/028432 dated Oct. 27, 2010.
Choe et al., "Chemistry and Reactions of Reactive Oxygen Species in Foods," Critical Reviews in Food Science and Nutrition, 46:1-22, 2006.
Gustavo et al., "Encapsulation Processes," pp. 199-219, 2006.
Livney et al., "Complexes and conjugates of biopolymers for delivery of bioactive ingredients via food," Delivery and Controlled Release of Bioactives in Foods and Nutraceuticals, pp. 234-250, 2008.
Pegg et al., "Encapsulation, Stabilization, and Controlled Release of Food Ingredients and Bioactives," Handbook of Food Preservation, pp. 509-568, 2007.
Office Action for Japanese Application No. 2012-502195 dated Jul. 23, 2014.
International Preliminary Report on Patentability for International Application No. PCT/US2010/028432 dated Sep. 27, 2011.

(Continued)

*Primary Examiner* — Micah-Paul Young
(74) *Attorney, Agent, or Firm* — Ratnerprestia

(57) ABSTRACT

The present invention relates to microparticles and methods of making such microparticles that protect a bioactive substance from heat, humidity and oxidation. A microparticle comprising a bioactive substance, an agglomerating agent, an emulsifier and solid fats is disclosed. A method to produce a microparticle comprising an agglomerated bioactive substance enrobed in a double layer of solid fats and emulsifier is also disclosed.

35 Claims, 3 Drawing Sheets

(56) References Cited

OTHER PUBLICATIONS

Supplementary European Search Report for Application No. EP 10 75 6764 dated Oct. 22, 2014.
Chinese Office Action for Application No. 201080021419.5 dated Oct. 8, 2014.
Japanese Office Action for Application No. 2012-502195 and English Translation, issued Apr. 2, 2015.
Fifth Chinese Office Action mailed Jul. 16, 2015 in Chinese Application No. 201080021419.5.
Japanese Office Action issued Aug. 14, 2015 in Japanese Application No. 2012-502195, including English translation.
Fourth Chinese Office Action for Application No. 201080021419.5, issued Apr. 14, 2015.
English translation of Fourth Chinese Office Action for Application No. 201080021419.5, issued Apr. 14, 2015.

* cited by examiner

MICROENCAPSULATION OF BIOACTIVE SUBSTANCES AND METHODS OF MAKING THE SAME

CROSS-REFERENCE TO RELATED APPLICATION

This application is filed under the provisions of 35 U.S.C. §371 and claims the priority of International Patent Application No. PCT/US2010/028432 filed on Mar. 24, 2010, which in turn claims priority to U.S. Provisional Application No. 61/163,728 filed in the United States Patent and Trademark Office on Mar. 26, 2009, the contents of which are hereby incorporated by reference herein for all purposes

BACKGROUND OF THE INVENTION

1. Field of the Invention

The present invention provides for microparticles and methods of making such microparticles for protecting encased bioactive substances from heat, humidity, oxidation and gastric incursions.

2. Related Background Art

A common difficulty associated with the incorporation of functional substances and/or drugs in food products is loss of activity with time, decomposition during the food manufacturing process and/or the destruction during passage of the product through the organism's digestive tract. The harsh environment of some food processes, like milling, mixing, baking, and extrusion, can destroy many bioactive substances before they become finished food products. This is especially true for enzymes and vitamins that are sensitive to most types of conventional food processing. Therefore, the food industry is continuously searching for new compositions and methods that protect bioactive compounds against decomposition during processing, storage, and gastric transit.

Additional problems result from the interaction between the desired bioactive compounds and other food components, such as metal chelators, surfactants, hygroscopic ingredients, etc. (Choe and Min, 2006). One method to protect and enhance the retention and appropriate release of a bioactive substance is encapsulation. Encapsulation is also used to protect the bioactive substance from oxygen, water, and light, as well as to convert the substance into a free-flowing powder that can be readily incorporated into various food products. Various attempts have been made over the years to enrobe or embed bioactive agents in many different types of biopolymers or synthetic polymers, including proteins, carbohydrates, and solid fats (Nissim G., 2008).

Most methods of encapsulation utilize water-soluble carrier substances such as proteins, sugars, modified starches, and gums (PCT/US2004/004003, WO2004/082660). Typical methods of encapsulation include spray drying, air suspension coating, spray cooling and chilling, co-crystallization, and centrifugal extrusion. However, these types of encapsulation are not suitable for protecting bioactive agents in food products that contain water or have a high water activity because of oxidation and subsequent degradation of the encapsulated bioactive substances under aqueous conditions. Since water is involved in the preparation of most foods at some stage of the food manufacturing process and storage, encapsulation in water-soluble polymers has limited applicability for improving the stability of bioactive compounds, or for controlling the retention of bioactive substances and directing their release in a programmed manner.

To overcome the problem of loss of activity during processing or storage in humid environments, fat encapsulation or top-coating of the water-soluble particles with a protective layer of solid fats is sometimes used. Proposed examples of coating methods with Solid Fats include: U.S. Pat. No. 4,350,679, which discloses the application of a carnauba wax coating on a soft gel. The functionality of the wax coating is to improve shell strength and moisture resistance as described in U.S. Pat. No. 5,789,014 wherein a wax, in powder or pellet form with a melting point between 40° C. and 50° C., was heated above its melting point and used for coating in a fluidized bed coating apparatus.

U.S. Patent Application Publication No. 2006/0051425 discloses methods for microencapsulation of active ingredients in a multilayer coat. The multilayer coat composed of various waxes and gums protects the active ingredient throughout processing, formulation, and storage, and enables a controlled release of the active ingredient. U.S. Patent Application Publication No. 2007/0042184 discloses a method of spray cooling aqueous beads comprising the active ingredient that is encapsulated in or by a hydrophobic shell matrix of solid fats. However, a major problem of these types of microencapsulation is that the coat is easily ruptured when water is added during conventional food manufacturing processes. Another problem with the use of fat coating is its limitation to food products that are processed at temperatures below the melting point of the fat. For example, this process is not applicable for a food process that includes boiling, baking, spray drying, or extruding, where temperatures well over 70° C. occur because the coating fat becomes liquefied and its protective properties are lost.

The object of this invention is to provide a composition and method of encapsulating a bioactive substance that overcomes these problems.

SUMMARY OF THE INVENTION

The invention disclosed herein, allows a high degree of loading of an active ingredient into a microparticle, which exhibits a high degree of resistance to heat and shear force, and a high degree of stability of the particle in high water activity environments is desired. Such microparticles also exhibit superior release kinetics in the absorptive or otherwise appropriate regions of the intestine, is particularly desired.

One aspect of the present invention provides a microparticle comprising a bioactive substance, an agglomerated agent, and a mixture of an emulsifier and edible solid fats.

A further aspect of the present invention provides a microparticle comprising a bioactive substance, an agglomerating agent and a mixture of an emulsifier and edible solid fats, wherein the agglomerated bioactive substance is enrobed in a double layer coating of an emulsifier and solid fats.

Yet another aspect of the present invention relates to microparticles comprising a mixture of a bioactive agent and agglomerating agent to form a bioactive agent containing core, wherein the bioactive agent containing core is encased in a first and second layer, and wherein the first layer is positioned adjacent to the bioactive agent core and comprising at least one emulsifier and the second layer positioned on the emulsifier layer comprising at least a solid fat compound.

A still further aspect of the present invention relates to a method of making free flowing solid microparticles comprising:

mixing a bioactive substance with an agglomerating agent;

forming bioactive substance/agglomerate microparticle cores;

contacting the cores with at least an emulsifier thereby forming a first layer encasing the cores; and contacting the first layer with at least one solid fat that solidifies on the surface of the layered cores.

The layers deposited on the bioactive core increase the size of the bioactive agglomerate core at least two times and more preferably from about 2 to 10 times the size of the bioactive agglomerate core. Preferably the microparticles are substantially spherical but other geometric shapes are also applicable including but not limited to rods, triangular, elliptical and multi-faceted.

Other aspects and features of the invention are described in more detail below.

DETAILED DESCRIPTION OF THE INVENTION

Definitions

Figure 1:
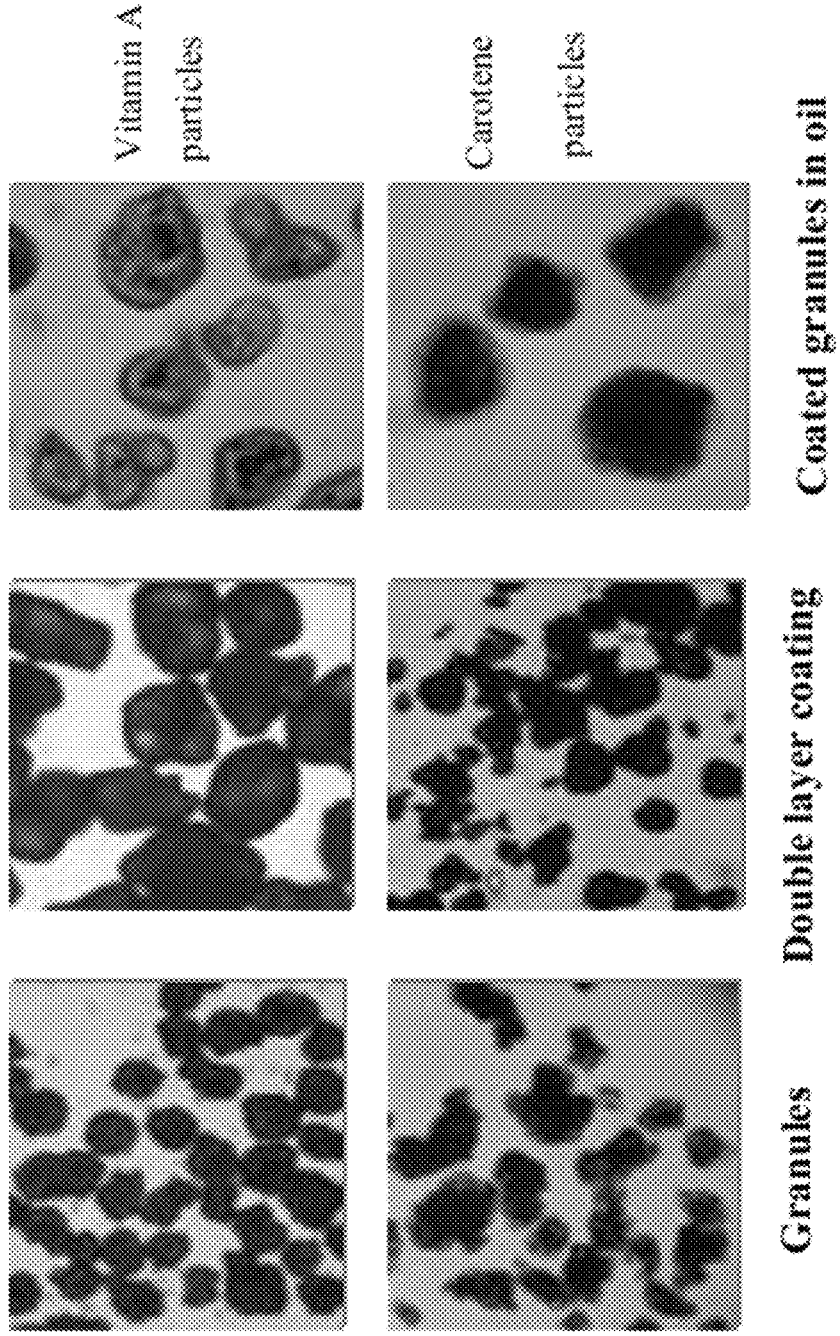
FIG. 1 shows the microscopic view (200x) of granulated particles containing a vitamin A or beta-carotene granules. Particles in oil were observed for integrity and stability (cracking) of the double layer coat.

"Microparticle" as used herein refers to a dry particle in a size range between 50-5000 micron comprised of an agglomerated bioactive substance enrobed in a double layer of emulsifier and solid fats. The microparticles encompass all microparticles of the invention, whether they are granules, beads, strands, particles, or any other solid accumulation.

"Bioactive Substances" broadly include any compound, or mixtures thereof, that can be delivered by the microparticles to produce a beneficial result in an organism to which the compound or mixture has been delivered. The Bioactive Substances can be living or dead microbes, bacteriophages and viruses, soluble or limited solubility compounds, such as an oil phase, powder, or other solid form. The term "bioactive" includes, but is not limited to, probiotic microbes, viruses, bacteriophages, liposomes, proteins or peptides (such as enzymes, vaccines, antibodies, antimicrobial peptides), antibiotics, pesticides, herbicides, germicides, biocides, algicides, rodenticides, fungicides, insecticides, antioxidants, plant and animal growth promoters, plant and animal growth inhibitors, preservatives, nutraceuticals, disinfectants, sterilization agents, catalysts, chemical reactants, fermentation agents, foods, animal feeds, food or animal feed supplements, nutrients, flavors, colors, dyes, cosmetics, drugs, vitamins, sex sterilants, fertility inhibitors, fertility promoters, air purifiers, microorganism attenuators, nucleic acids (e.g., RNA, DNA, Peptide Nucleic Acid, vectors, plasmids, ribozymes, aptamers, dendrimers, and the like), and other agents that provide improved activity at the site of action.

"Agglomeration" as used herein refers to a process of transforming fine particles into larger particles by the addition of an agglomerating agent and introduction of an external force. Methods of agglomeration may include spray drying, pan coating and spinning disk encapsulation (also known as rotational suspension separation encapsulation), supercritical fluid encapsulation, air suspension agglomeration, fluidized bed agglomeration, spray cooling/chilling (including matrix particulation), extrusion, centrifugal extrusion, pellet mill, prilling, hydrogel spray capture and other methods of agglomeration known in the art.

"Agglomeration agent" as used herein refers to any additive to the bioactive substance being agglomerated that produce bonding strength in the agglomerated particle. An agglomeration agent can be a liquid or solid that forms a bridge, film or matrix filler or that causes a chemical reaction. Examples may include water solutions, carbohydrates, proteins and any combination thereof. The carbohydrates may be any sugar or composed of longer chains of monosaccharide units. Simple carbohydrates include, but are not limited to, mono and disaccharides glucose, fructose, galactose, sucrose, lactose, maltose, maltodextrin and trehalose. Complex carbohydrates include, but are not limited to, agar, alginate, arabinoxylan, carrageenan, carboxymethylcellulose, cellulose, chitosan, curdlan, b-glucan, guar gum, gum arabic, locust bean gum, lignin, pectin, xanthan gum, and starches (natural or modified). The protein may be any suitable protein of animal or vegetable origin include, but are not limited to, gelatins, milk proteins, zein proteins, soy proteins, wheat proteins (natural, isolates, modified or hydrolyzed).

"Solid Fats" as used herein are any lipid or a mixture of lipids that turn into a solid form at the final temperature that the microparticles or the food product containing the microparticles are stored and broadly include, but are not limited to, any oils and fats from plants, algae, fungi, yeast, bacteria, or animals and/or hydrocarbon products whether natural or made by chemical means. Solid animal oils and fats include: beef tallow (mp 35-38° C.), mutton tallow (mp 40-45° C.), butter, cholesterol esters, stearine (mp 49-75° C.) and stearic acid (mp 71° C.). Solid vegetable oils include: hydrogenated oil, coconut oil, coconut butter, cocoa butter, cocoa butter equivalents, and phytosterol esters. Natural waxes include: carnauba wax (mp 78-81° C.), candelilla wax (mp 68° C.), beeswax (mp 60-63° C.), spermaceti-sperm oil (mp 42-49° C.), japan wax, jojoba oil and hardened jojoba oil (mp 30-40° C.). Hydrocarbons (unsaponifiable) include: paraffin wax (mp 35-36 C), montan wax (mp 76-84° C.), Ceresine wax (mp 60-85° C.). The final melting point of lipids can be manipulated through mixing two or more lipids of different melting points. Liquid oils can be converted into solid fats at about room temperature through hydrogenation and can be used either alone or in a mixture with other liquid or solid lipids provided that the final lipid is solid at the temperature that the microparticles or the food product containing the microparticles is maintained.

"Emulsifiers" as used herein refers to a molecule made up of a lipophilic component and a hydrophilic component. Typical examples of emulsifiers are lecithins, monoglycerides, diglycerides, phosphated monoglycerides, esters of monoglycerides, succinic acid esters of monoglycerides, diacetyl tartaric acid esters of monoglycerides, sucrose esters of fatty acids, propylene glycol esters of fatty acids, sorbitan esters of fatty acids, polyglycerol esters of fatty acids.

"Antioxidants" as used herein refer to compounds that interrupt the free radical reaction chain. Typical examples of such antioxidants are amino acids (e.g., glycine, histidine, tyrosine, tryptophan) and derivatives thereof, carotenoids (e.g., astaxanthin, zeaxanthin, lutein, etc), carotenes (e.g., α-carotene, β-carotene, lycopene, etc.) and derivatives thereof, lipoic acid and derivatives thereof (e.g., dihydrolipoic acid), chelators (e.g., α-hydroxy fatty acids, palmitic acid, phytic acid, lactoferrin, etc), α-hydroxy acids (e.g., citric acid, lactic acid, malic acid, etc), humic acid, bile acid, bile extracts, bilirubin, biliverdin, EDTA, EGTA and derivatives thereof, folic acid and derivatives thereof, ubiquinone and ubiquinol and derivatives thereof, vitamin C and derivatives thereof (e.g., ascorbyl palmitate, Mg ascorbyl phosphate, ascorbyl acetate, etc.), tocopherols and derivatives (e.g., example vitamin E acetate), vitamin A and derivatives (e.g., vitamin A palmitate), zinc and derivatives thereof (e.g., $ZnSO_4$), selenium and derivatives thereof (e.g., selenium methionine) and natural antioxidants (e.g., rosemary, sage, oregano, thyme, ginger, summer savory, black pepper, red pepper, clove, marjoram, basil, peppermint, spearmint, common balm, fennel, parsley, cinnamon, cumin, nutmeg, garlic, coriander).

The present invention provides compositions and methods to produce said compositions that protect a bioactive substance during food processing and storage. In particular, the invention provides a microcapsule comprising a core consisting of an agglomerating agent and a bioactive substance that is surrounded by a double layer of an emulsifier and solid fats. It was unexpectedly found that a bioactive substance that is protected in a core particle and coated with a double layer composed of an emulsifier-rich inner layer and a solid fat outer layer, is remarkably stable and remains intact in both hydrophilic and hydrophobic phases.

One aspect of the invention is a composition comprising a bioactive substance and an agglomerating agent, wherein the concentration of the agglomerating agent in the composition is from about 1% to about 50% by weight of the bioactive substance. In a preferred embodiment, the concentration of the agglomerating agent in the composition is from about 2% to about 20% by weight of the bioactive substance. A variety of bioactive substances are suitable for use in this invention. In general, the bioactive substance comprises at least one bioactive substance. A variety of agglomerating agents are suitable for use in this invention. In general, the agglomerating agent comprises at least one carbohydrate or protein. The carbohydrate can be a simple carbohydrate or a complex carbohydrate composed of longer chains of sugars. The protein may be any suitable protein of animal or vegetable origin (natural, isolates, modified or hydrolyzed).

To prepare the composition, a carbohydrate or protein solution is contacted with a bioactive substance to form dry agglomerated microparticles in a size range from 50-5000 micron. The agglomerated microparticles are then dried by techniques well known in the art, such as hot air drying, spray drying, freeze drying, or vacuum evaporation. The agglomerated particle is then coated with a double layer consisting of an emulsifier-rich inner layer and solid fat-rich outer layer. Typical microparticles of the present invention are presented in FIG. 1.

A variety of emulsifiers are suitable for use in this invention. In one embodiment, the emulsifier may be a mixture of phospholipids, such as lecithin. Commercial sources of lecithin include soybeans, rice, sunflower seeds, egg yolks and milk fat. Lecithin may be de-oiled and treated such that it is an essentially pure mixture of phospholipids. Lecithin may also be modified to make the phospholipids more water-soluble. Modifications include hydroxylation, acetylation, and enzyme treatment, in which one of the fatty acids is removed by a phospholipase enzyme and replaced with a hydroxyl group.

A variety of solid fats are suitable for use in this invention. In general, the solid fats can be simple animal or plant solid oils and fats and natural waxes. In a preferable embodiment the melting point of the solid fat is at least 40° C. and preferable above 60° C. The final melting point of the solid fats can be manipulated through mixing two or more fats with different melting points. Liquid oils can be converted into solid fats through hydrogenation and can be used either alone or in a mixture with other liquid or solid fats provided that they form a free flowing powder at the temperature that the microparticles or the food product containing the microparticles is maintained.

The composition may also consist of an antioxidant to further stabilize the bioactive substance and to prevent its oxidation. A variety of antioxidants are suitable for use in this invention. The concentration of the antioxidant may range from about 0.001% to about 1% by weight in the agglomerated particle, and from about 0.01% to about 10% by weight in the inner layer.

In additional embodiments, binders and lubricants may also be included in the double layer coating. Examples include stearic acid, magnesium stearate, calcium stearate or other metallic stearate, talc, waxes and glycerides, light mineral oil, PEG, glyceryl behenate, colloidal silica, corn starch, polyethylene glycols, alkyl sulfates, sodium benzoate, sodium acetate etc.

The ratio of the emulsifier to the solid fats in the double layer will vary depending upon the nature of the emulsifier and the solid fats. In particular, the concentration of emulsifier in the inner layer will be of a sufficient amount required to maintain the firmness of the inner layer at the temperature that the microparticles or the food product containing the microparticles is maintained. The concentration of the emulsifier will generally range from about 5% to about 50% by weight of the inner layer. In one embodiment, the concentration of the emulsifier may range from about 5% to about 30% by weight of the inner layer. In another embodiment, the concentration of the emulsifier may range from about 5% to about 20% by weight of the inner layer. In a preferred embodiment, the concentration of the emulsifier may range from about 20% to about 40% by weight of the inner layer.

In a particular embodiment, the melting temperature of the outer layer is substantially higher than the melting temperature of the inner layer. Specifically, the outer layer is predominantly composed of solid fats having high melting temperature. In a preferred embodiment, the outer layer is composed of hydrogenated oil, natural or hydrocarbon waxes having a melting point from about 55° C. to about 85° C.

The microparticle of the present invention is generally formed by first agglomerating the bioactive substance to convert finely particulate substances to a desired average particle size that allows for top coating. While some particulate substances exhibit an inherent tackiness or adhesive character, adequate to provide the particle adherence necessary for agglomeration, it has long been the practice to contact substance with a solution containing agglomerating agents, in such manner as to promote particle adherence when a mass of the particles is agitated. The agglomerating agent solution is usually introduced as a spray or mist, followed by drying of the agglomerated product to remove the moisture added for agglomeration.

A preferred agglomerating agent in this invention is carbohydrates or proteins. Non-limiting examples of carbohydrates include sugars, starches, gums or combinations thereof. Non-limiting examples of proteins include gelatins, milk proteins, zein proteins and vegetable proteins or combinations thereof. In some embodiments, at least one antioxidant may be added to the mixture. In embodiments comprising simple carbohydrates, a solution may be formed comprising from about 5% to 50% sugars. In one embodiment, the concentration of the simple carbohydrates in the solution may range from about 20% to about 30% by weight. In embodiments comprising complex carbohydrates, a solution may be formed consisting of from about 0.5% to 10% complex carbohydrates. In one embodiment, the concentration of the complex carbohydrates in the solution may range from about 1% to about 5% by weight. In embodiments comprising proteins, a solution may be formed comprising from about 1% to 5% proteins. In a preferred embodiment, the agglomerating solution is a mixture of simple carbohydrates and complex carbohydrates and may further include at least one additional antioxidant.

To make the agglomerated microparticles, the agglomerating agent solution is usually introduced as a spray or mist and allows contacting with the agitated bioactive substance and to form agglomerated microparticles in a size range from 50-5000 micron. The agglomerated microparticles are then dried by techniques well known in the art, such as air-drying, spray drying, freeze drying, or vacuum evaporation. The resultant agglomerated microparticles are substantially water-free. The bioactive substance is now partly stabilized in the carbohydrate and an antioxidant complex, but still readily soluble upon intact with water.

To provide a substantially water resistant environment and heat protection for the composition of the present invention, a double layer coating consisting of an emulsion rich inner layer and solid fats rich outer layer is used. In one embodiment, the concentration of the emulsifier in the inner layer will be in a sufficient amount to provide a solid layer at the temperature that the microparticles or the food product containing the microparticles is maintained. In one embodiment, the inner layer is a substantially water-free composition and comprises a mixture of solid fats, emulsifier, and antioxidant. In a preferred embodiment, the inner layer comprises hydrogenated oil or natural wax, lecithin or monoglycerides, and tocopherols or herb extracts. The oil mixture is heated slightly above its melting point and sprayed over the agglomerated microparticles under constant agitation. The inner layer coat is applied until the total mass of the microparticles has increased by 10% to 25% of their initial weight. In one preferred embodiment, the inner layer coat is applied until the total mass of the microparticles has increased by 15% to 20% of their initial weight.

In still another embodiment, a substantially water-free outer layer is provided. The outer layer coat comprises edible high melting point solid fats. The melting temperature of the outer layer is substantially higher than the melting temperature of the inner layer. In a preferred embodiment of the invention, the outer layer is composed of hydrogenated oil, natural waxes, or hydrocarbon waxes having a melting point from about 60° C. to about 85° C. In an especially preferred embodiment, the edible solid fat is combined with a plasticizer (e.g., stearic acid, magnesium stearate, calcium stearate or other metallic stearate, talc, waxes and glycerides, light mineral oil, PEG, glyceryl behenate, colloidal silica, corn starch and starch derivatives, polyethylene glycols, alkyl sulfates, sodium benzoate, sodium acetate, etc). The solid fat mixture is heated to slightly above its melting point and uniformly sprayed over the inner layer coated agglomerated microparticles under constant agitation. The outer layer coat is applied sequentially on top of the inner layer until the total mass of the microparticles increased by 20% to 60% of their initial weight. In a preferred embodiment, the outer layer coat is applied until the total mass of the microparticles increased by 30% to 50% of their initial weight.

Figure 2:
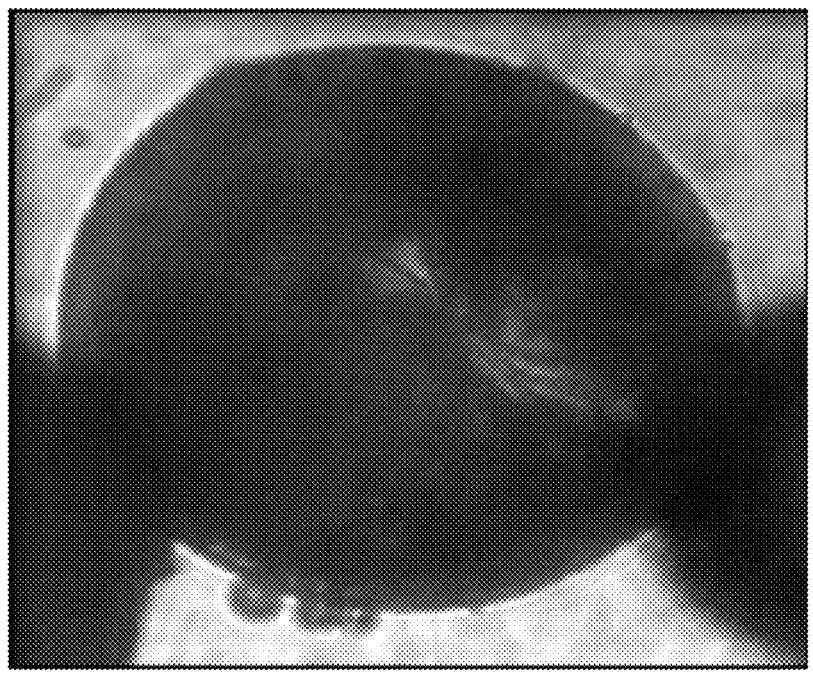
FIG. 2 shows the microscopic view (400x) of coated microparticles prepared with and without an inner layer emulsifier after 2 hours mixing in oil exemplifying the value of the emulsifier layer in the prevention of cracking of the particles.
Figure 2:
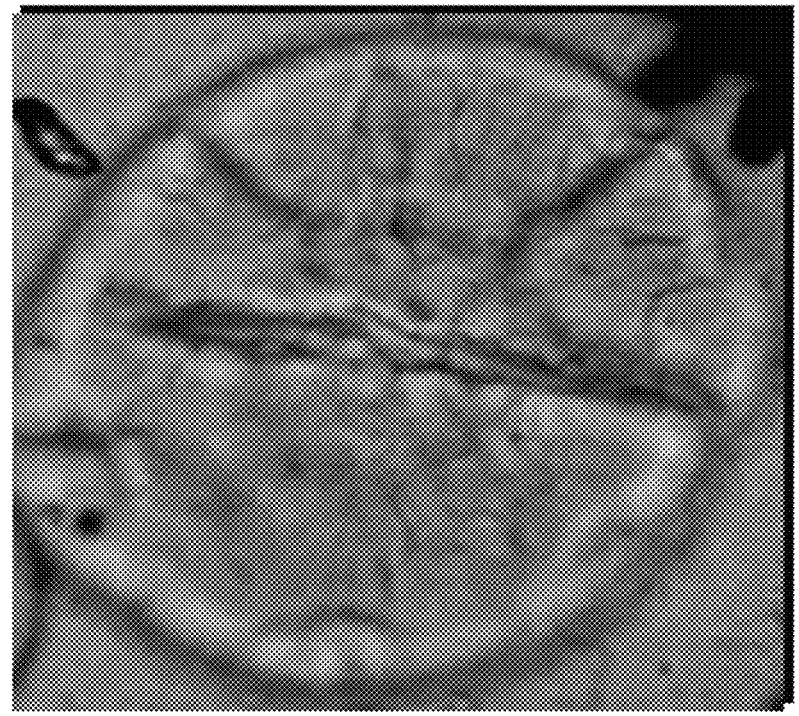

Without being bound by any particular theory, the double layer coat renders the microparticle water-insoluble and rupture resistant. FIG. 2 demonstrates the effect of the emulsifier-rich inner layer coat on the stability of the particle. When the microparticle is used in food processing which involves high water activities, the double layer coat serves as a substantial barrier to moisture, thereby protecting and stabilizing the core bioactive substance. It also preserves and protects the bioactive substance from heat and shear exposures that accompany dough preparation and baking Under such conditions, the layers will melt and collapse upon the core bioactive substance (i.e., the carbohydrate complex) and thus still provide substantial protection from heat and moisture.

Several methods may be employed to create the microparticle of the present invention. Methods of agglomeration may include spray drying, pan coating and spinning disk encapsulation (also known as rotational suspension separation encapsulation), supercritical fluid encapsulation, air suspension agglomeration, fluidized bed agglomeration, spray cooling/chilling (including matrix particulation), extrusion, centrifugal extrusion, hydrogel spray capture and other methods of agglomeration known in the art.

In one aspect of the present invention, the same encapsulation method may be employed sequentially to produce the microparticle of the present invention. Such an encapsulation method may utilize rotational suspension or air suspension process in which the bioactive substance is first agglomerated while rotated or suspended in an upward-moving air stream, dried with a heated stream of air and then the double layer coat is applied, starting with emulsifier-rich inner layer and applying sequentially the final high melting point solid fat outer layer. Methods of rotational and air suspension encapsulation are well known in the art. (Gustavo et al., 2006; Shafiur R. M. 2007).

In one aspect of the present invention, the microparticles may be used in any food product such as, but not limited to, dairy or liquid beverage food products (e.g., yogurt, cheese, ice cream, whipping cream, sour cream, milk, soy milk, rice milk, fruit and vegetable drinks, nutritional drinks, energy drinks and liquid infant formula), dry baked products (e.g., breakfast cereals, potato chips, breads, cakes, pies, cookies, biscuits, granola bars, nutrition bars, chocolate products, nutritional supplements and pharmaceutical preparations), and meat, including processed meat and meat analog products. The food product may also be a canned food product to which the bioactive substance microcapsules are added.

In yet another embodiment, the microparticles of the present invention may be used in feed products for animals. The animal may be a companion animal, an agricultural animal, or an aquatic organism. The feeds may be pelleted, extruded, spray coated, top coated or formed by any other methods.

As various changes could be made in the above composition, products and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Fluidized Bed Preparation of Vitamin A Microparticles

An agglomerating solution was prepared by dissolving 10 g sucrose and 1 g gum acacia in 100 g warm water (40-60° C.). To this was added 50 mg of sodium citrate and the solution cooled to room temperature. In a modified fluid bed dryer/granulator/coater system (Fluid Air model 2, 2 liter max working capacity), equipped with air blower, variable air velocity and variable heat control, 1000 g of fine powder Vitamin A palmitate (BASF, Florham Park, N.J., particle size range from 0.5 micron to 10 micron) was agglomerated by top spraying the agglomeration solution in fine mist for about 5 minutes with a two-fluid nozzle at an air pressure of 20 psi and a liquid rate of about 4 ml/min. The resulting agglomerated particles were air dried in the fluidized bed dryer to a residual moisture level of less than 3 percent using a drying temperature in the range of 50° C. to 60° C. The double layer coat was then applied starting with top spraying the emulsifier-rich inner layer until the mass of the particles increased by 20% of their original mass. The inner layer was composed of 40% (w/w) soy lecithin (Archer Daniels Midland Company, Decatur, Ill.), 55% (w/w) hydrogenated soy oil (17 Stearine, Loders Croklan, Channahon, Ill.) and 5% (w/w) of Rosemary extract (OxyLess, Naturex, Mamaroneck, N.Y.). The solid fat-rich outer layer was then applied sequentially until the mass of the particles increased by 40% of their original mass. The outer layer was composed of 100% hydrogenated palm oil (27 Stearine, Loders Croklan, Channahon, Ill.). The temperature of the hydrogenated palm oil was maintained at 70° C. throughout the spraying process and the particle temperature was maintained at about 40° C. The final step involved cooling the microparticles, collecting and sieving the microparticles to a size range between 50 and 450 micron. FIG. 1 shows typical microparticles of the present invention and their retention stability in oil solution.

The microparticles may also be produced in a batch process where the dried agglomerated microparticles are harvested and sieved to the desired size and then returned to the fluidized bed drier for coating.

Example 2

Pan Coating Preparation Method of Vitamin A Microparticles

Using a coating pan such as is commonly used in the pharmaceutical industry to coat tablets, a Vitamin A palmitate (BASF, Florham Park, N.J.) was agglomerated with the agglomeration solution described in example 1. The pan was set to rotate at 60 to 75 RPM. A two-fluid nozzle was connected to a hot air supply which was regulated between 15 to 25 psi. Lecithin, (400 g) and OxyLess (50 g) were dissolved in 550 g of 17-stearine at 75° C. The molten lecithin/Antioxidant/Solid Fat-solution was supplied to the liquid side of the nozzle at a rate of about 6 ml/min. Warm air (40° C.) was blown into the pan to help facilitate a uniform coating. The lecithin/Antioxidant/Solid Fat-solution was sprayed until 15% of inner layer coating was deposited. The coating solution was then changed to 100% molten 17-stearine and additional 30% of outer layer coating applied. The microparticles were then allowed to cool to room temperature and sieved, collecting a microparticle fraction between 50 and 450 µm.

The microparticles can also be produced in a batch process were the dried agglomerated particles are harvested and sieved to the desired size and then returned to the coating pan for coating.

Example 3

Encapsulation of Vitamins A, D3 and K1 Mixture in Microparticles

A vitamins mixture containing 92% Vitamin A palmitate, 0.5% Vitamin $D_3$ and 7.5% vitamin $K_1$ (commercially available from Sigma-Aldrich Co., St. Louis, Mo.) was agglomerated and double layer coated in a fluidized bed drier or coating pan as described in examples 1 or 2. The agglomeration solution composed of 10% (w/w) maltodextrin, 2% (w/w) carboxymethylcellulose and 0.5% (w/w) BHT. The inner layer was composed of 40% (w/w) soy lecithin, 50% (w/w) of 17-stearine and 10% (w/w) of OxyLess. The outer layer was composed of 90% (w/w) of 27-stearine and 10% (w/w) beeswax (Frank B. Ross Co.—Rahway, N.J.).

Example 4

Encapsulation of Iron Mineral in Microparticles

Ferrous sulfate (commercially available from Sigma-Aldrich Co., St. Louis, Mo.) was agglomerated and double layer coated in a fluidized bed drier or coating pan as described in examples 1 or 2. The agglomeration solution composed of 10% (w/w) maltodextrin, 2% (w/w), sodium alginate and 0.5% (w/w) Ascorbic acid (all from Sigma-Aldrich Co., St. Louis, Mo.). The inner layer was composed of 40% (w/w) monoglycerides (Cognis GmbH Manheim, Germany), 50% (w/w) of 17-stearine and 10% (w/w) α-tocopheryl acetate (Sigma-Aldrich Co., St. Louis, Mo.). The outer layer was composed of 90% (w/w) of 27-stearine and 10% (w/w) beeswax (Frank B. Ross Co.—Rahway, N.J.).

Example 5

Encapsulation of Digestive Enzymes in Microparticles

Pancreatin (commercially available from Sigma-Aldrich Co., St. Louis, Mo.) was agglomerated and double layer coated in a fluidized bed drier or coating pan as described in Examples 1 or 2. The agglomeration solution was composed of 10% (w/w) maltodextrin, 2% (w/w), gum acacia and 0.5% (w/w) ascorbic acid (all from Sigma-Aldrich Co., St. Louis, Mo.). The inner layer was composed of 30% (w/w) lecithin (Archer Daniels Midland Company, Decatur, Ill.), 60% (w/w) hydrogenated soy oil (17 Stearine, Loders Croklan, Channahon, Ill.) and 10% (w/w) Rosemary extract (Oxy- Less, Naturex, Mamaroneck, N.Y.). The outer layer was composed of 100% hydrogenated palm oil (27 Stearine, Loders Croklan, Channahon, Ill.).

Example 6

Encapsulation of the Protein Hormone Leptin in Microparticles

Leptin (commercially available from Sigma-Aldrich Co., St. Louis, Mo.) was agglomerated by a solution containing 1% (w/w) chitosan and 1% (w/w) alginate. The agglomerated particles were double layer coated in a fluidized bed drier or coating pan as described in Examples 1 or 2. The inner layer was composed of 30% (w/w) lecithin (Archer Daniels Midland Company, Decatur, Ill.), 60% (w/w) hydrogenated soy oil (17 Stearine, Loders Croklan, Channahon, Ill.), 5% (w/w) Rosemary extract (OxyLess, Naturex, Mamaroneck, N.Y.) and 5% α-tocopheryl acetate. The outer layer was composed of 100% hydrogenated palm oil (27 Stearine, Loders Croklan, Channahon, Ill.).

Example 7

Encapsulation of a Vitamin B Complex in Microparticles

A powder mix of vitamin B complex containing vitamin B1 (Thiamine HCL), vitamin B2 (Riboflavin), vitamin B6 (Pyridoxine HCL), vitamin B12 (Cyanocobalamin), calcium pantothenate, folic acid, biotin, Choline and Inositol (all commercially available from Sigma-Aldrich Co., St. Louis, Mo.) were agglomerated and double layer coated in a coating pan as described in Example 2. The powder mix was agglomerated until spherical particles in a size range between 500 and 1000 micron were obtained. The agglomeration solution was composed of 5% (w/w) sodium caseinate, 2% (w/w) gum acacia and 0.5% (w/w) Ascorbic acid (all from Sigma-Aldrich Co., St. Louis, Mo.). The inner layer was composed of 40% (w/w) monoglycerides (Cognis GmbH Manheim, Germany), 50% (w/w) of 17-stearine and 10% (w/w) α-tocopheryl acetate (Sigma-Aldrich Co., St. Louis, Mo.). The outer layer was composed of 90% (w/w) of 27-stearine and 10% (w/w) beeswax (Frank B. Ross Co.—Rahway, N.J.).

Example 8

Release Kinetics of Carotenes from Microparticles in Oil

To demonstrate the protection of a carotene in the microparticles of the present invention, natural astaxanthin (Cyanotech, Kailua-Kona, Hi.) was encapsulated as described in Example 2. Microparticles were mixed in vials containing soy oil at low (0.5 g/10 ml) and high (1 g/10 ml) concentrations and shaken at 150 RPM for 1 or 2.5 hours and the $OD_{475}$ of filtered oil were measured. Table 1 shows the release of the pigment to the oil solution from non-coated and coated granules. The carotenoid was completely released to the oil from non-coated particles, but was entirely retained in the double coated particles. The carotene was completely released from the double coated granules only after a short exposure to high temperature (100° C.).

TABLE 1

| Treatment | 1 hr at 20° C. | 2.5 hr at 20° C. | 2 min at 100° C. |
|---|---|---|---|
| Uncoated (0.5 g/10 ml oil) | 0.90 | 1.34 | >2.00 |
| Uncoated (1.0 g/10 ml oil) | 1.84 | >2.00 | >2.00 |
| Coated (0.5 g/10 ml oil) | 0.07 | 0.09 | 1.84 |
| Coated (0/5 g/10 ml oil) | 0.14 | 0.19 | >2.00 |

Release kinetics of non-encapsulated and encapsulated carotenes (astaxanthin) in soy oil measured by optical density at 475 nm. Encapsulated particles retained the carotenes 10-fold better than non-encapsulated granules. Following heat exposure, carotenes were completely released from microcapsules

Example 9

Figure 3:
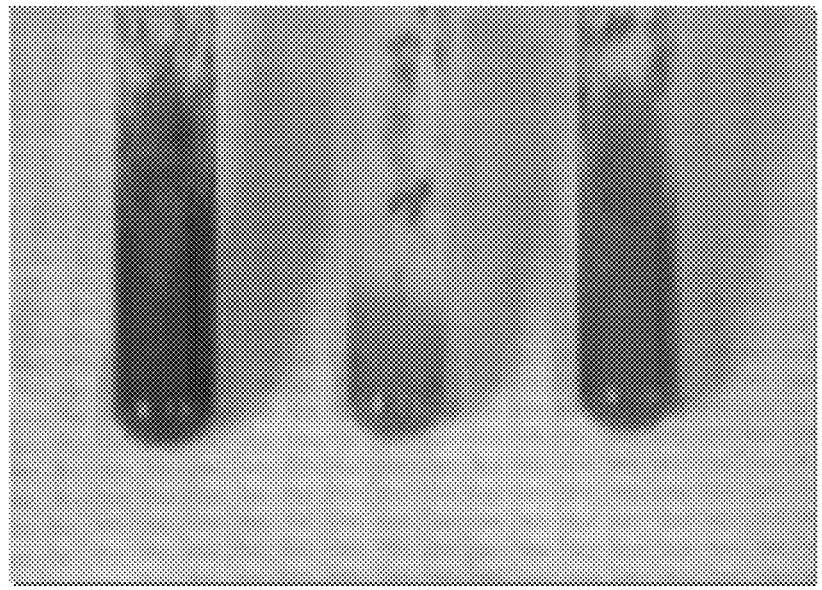
FIG. 3 shows the release of a carotene pigment from coated or uncoated granules in simulated gastric (pH-2) and intestinal juices (pH-7.4). (A) Non-coated particles were completely dissolved in gastric juice and released their carotene payload into the gastric solution. (B) Coated granules protected the carotene in the gastric juice but (C) completely dissolved in intestinal juice releasing the pigment into the intestinal solution. Particles were incubated for 2 hours at 37° C. in simulated gastric juice (pH 2) or intestinal juice (pH 7.4).

Release Kinetics and Gastric Protection of Carotene Microparticles in Digestive Juices To demonstrate the protection of a carotene in the microparticles of the present invention, coated and non-coated granules of natural astaxanthin were produced as described in Examples 2 and 6. The granulating solution comprised of 2% sodium alginate and 10% maltodextrin. Microparticles were mixed in vials containing simulated gastric juice (pH-2) and simulated intestinal juice (pH-7.4) and incubated at 37° C. for 2 hours. FIG. 3 shows the release of the carotene into the digestive juices. While the carotene was released from non-coated granules in both digestive juices, it was contained within the double layer coated granules in the gastric juices but completely released in intestinal juice. This experiment demonstrates the gastric protection of the encapsulation system of the present invention.

Example 10

Stability of Double Layer Coated Granules of Vitamin A in Baked Cookies

To demonstrate the protection of vitamin A, microparticles of the present invention in baked cookies, vitamin A palmitate (BASF, Florham Park, N.J.) was granulated and double layer coated as described in Example 3. Coated and non-coated granules were mixed in Betty Crocker cookie flour (General Mills Inc., Minneapolis, Minn.) at equal concentrations of 850 IU/g and cookies prepared and baked according to the manufacturer's instruction, that being at 200° C. for 20 minutes. The vitamin A contents in the baked cookie samples are shown in Table 2. The concentration of vitamin A in baked cookies containing non-coated granules was 30% less than its initial prebaking concentration, while in baked cookies containing double layer coated granules the concentration of vitamin A exhibited no loss of Vitamin A as shown in Table 2. The non-coated granules lost 30% of vitamin A after baking, while the double coated granules retained 100% of the vitamin A.

TABLE 2

|  | Uncoated Granules | Double Coated Granules |
|---|---|---|
| Starting Dough | 850 | 850 |
| After Baking | 594 | 855 |

REFERENCES

The contents of all reference cited herein are hereby incorporated by reference herein for all purposes.

Choe E, Min D. B. 2006. Chemistry and reactions of reactive oxygen species in foods. Crit Rev Food Sci Nutr. 46(1):1-22.

Nissim G., 2008. Delivery and Controlled Release of Bioactives in Foods and Nutraceuticals. Woodhead Publishing Ltd., Cambridge, UK.

Shefer, A. and S. Shefer, A controlled release system for pharmaceutical food and nutraceutical use, in PCT/US2004/004003, WO 2004/082660 A1. 2004, Salvona LLC.

Mizuno Y and K. M., Soft capsule coated with a film of carnauba wax and process for the preparation of the same, in U.S. Pat. No. 4,350,679. 1982.

Maruyama, N., Y. Nishiyama, and H. Kokubo, Method of manufacturing a solid preparation coated with non-solvent coating, in U.S. Pat. No. 5,789,014. 1996.

Kamel A, et al., Wax-encapsulated particles, in U.S. Pat. No. 5,258,132. 1993.

Kvitnitsky, E. Shapiro, Y. Privalov, O. Oleinik, I. and Polisher, I., Method of microencapsulation, in US20060051425. 2005.

Coyne, B. Faragher, J. Gouin, S. Hansen, C. B. Ingram, R. Isak, T. Thomas, L. V. Tse, K. L. Microcapsules, US20070042184. 2004.

Gustavo, V. Cánovas, B. Ortega-Rivas, E. Juliano, P. and Yan, H. 2006. Food Powders Physical Properties, Processing, and Functionality. Springer. Norwell, Mass. US.

Shafiur, R. M. 2007. Handbook of Food Preservation. CRC Press, Klagenfurt, Australia.

What is claimed is:

1. A microparticle comprising a core, a first layer on the core, and a second layer on the first layer, the core comprising a mixture of a bioactive substance and an agglomerating agent; the first layer comprising at least one emulsifier, and the second layer comprising at least one edible solid fat, the second layer being formed by melt coating;
   wherein the melting temperature of the second layer is higher than the melting temperature of the first layer;
   wherein the core is encased in the first and second layers, and the core is a dried but previously aqueous mixture comprising the bioactive substance and the agglomerating agent in which the agglomerating agent forms a bridge, film or matrix filler that produces bonding strength within the core;
   wherein the at least one emulsifier is selected from the group consisting of mono and di-glycerides, phospholipids, egg or soy lecithin, sucrose fatty acid esters, polyglycerol fatty acid esters and combinations of these.

2. The microparticle of claim 1, wherein the bioactive substance is soluble in either water or oil.

3. The microparticle of claim 1, wherein the bioactive substance is selected from the group consisting of vitamins, minerals, proteins, enzymes, essential amino acids, essential fatty acids and combinations of these.

4. The microparticle of claim 1, wherein the agglomerating agent is selected from the group consisting of carbohydrates, proteins, and combinations of these.

5. The microparticle of claim 4, wherein the agglomerating agent is a carbohydrate selected from the group consisting of glucose, fructose, galactose, sucrose, lactose, maltose, dextrose, starches, glycogen, gums and combinations of these.

6. The microparticle of claim 4, wherein the agglomerating agent is a protein selected from the group consisting of animal proteins, milk proteins, zein proteins, vegetable proteins, protein isolates, protein hydrolyzates and combinations of these.

7. The microparticle of claim 1, wherein the at least one edible solid fat is selected from the group consisting of hydrogenated animal or vegetable oils, waxes and mixtures thereof.

8. The microparticle of claim 1, wherein the microparticle further comprises an antioxidant, other than the at least one emulsifier, selected from the group consisting of tocopherols, ascorbyl palmitate, lipoic acid, carotenoids, phyto-nutrients, herbs extracts and mixtures thereof.

9. The microparticle of claim 1, wherein the agglomerating agent comprises at least one carbohydrate and wherein the concentration of the bioactive substance in the microparticle is from about 1% to about 70% by weight thereof.

10. The microparticle of claim 9, wherein the concentration of the at least one carbohydrate is from about 1% to about 50% by weight of the bioactive substance.

11. The microparticle of claim 1, wherein the first and second layers are present in an amount such that the size of the microparticle is from 2 to 10 times the size of the core.

12. The microparticle of claim 1, wherein the concentration of the emulsifier in the first layer is from about 5% to about 50% by weight.

13. The microparticle of claim 9, wherein the microparticle further comprises an antioxidant selected from the group consisting of tocopherols, ascorbyl palmitate, lipoic acid, carotenoids, phyto-nutrients, herb extracts and mixtures thereof.

14. A method of making free flowing solid microparticles, comprising in sequence:
   contacting a bioactive substance with an agglomerating solution comprising water and an agglomerating agent and then drying to form microparticle cores in which the agglomerating agent forms a bridge, film or matrix filler that produces bonding strength within the cores;
   contacting the cores with a composition comprising at least one emulsifier, thereby forming a first layer encasing each of the cores; and
   forming on the first layer, by melt coating, a second layer that comprises at least one solid fat;
   wherein the melting temperature of the second layer is higher than the melting temperature of the first layer; and
   wherein the cores are encased in the first and second layers and the emulsifier is selected from the group consisting of mono and di-glycerides, phospholipids, egg or soy lecithin, sucrose fatty acid esters, polyglycerol fatty acid esters and combinations of these.

15. The method of claim 14, wherein the cores are produced by agglomerating or spray drying a mixture of the bioactive substance and agglomerating agent to form agglomerated particles, and sieving the agglomerated particles to a desired size.

16. The method of claim 14, wherein the size of the microparticle cores is 50-5000 microns.

17. The method of claim 14, wherein the bioactive substance is selected from the group consisting of vitamins, minerals, proteins, enzymes, essential amino acid, essential fatty acids and combinations of these.

18. The method of claim 14, wherein the agglomerating agent is selected from the group consisting of carbohydrates, proteins, and combinations of these.

19. The method of claim 14, wherein the at least one solid fat is selected from the group consisting of hydrogenated animal of vegetable oils, waxes and mixtures thereof.

20. The method of claim 14, wherein the microparticle further comprises an antioxidant, other than the emulsifier, selected from the group consisting of tocopherols, ascorbyl palmitate, lipoic acid, carotenoids, phyto-nutrients, herbs extracts and combinations of these.

21. The method of claim 14, wherein the concentration of the agglomerating agent is from about 1% to about 50% by weight of the bioactive substance.

22. The method of claim 14, wherein the concentration of the emulsifier in the first layer is from about 5% to about 50% by weight thereof.

23. The method of claim 14, wherein the concentration of the at least one solid fat in the second layer is from about 70% to about 100% by weight of the second layer.

24. The method of claim 14, wherein the first and second layers are present in an amount such that the size of the microparticles is from 2 to 10 times the size of the cores.

25. The microparticle of claim 1, wherein the concentration of the at least one edible solid fat in the second layer is from about 70% to about 100% by weight of the second layer.

26. A food or feed product prepared with the microparticle of claim 1.

27. The food or feed product of claim 26, wherein the food or feed product is a baked, pelleted or extruded product.

28. The microparticle of claim 1, wherein the first layer further comprises a fat.

29. The method of claim 14, wherein the composition further comprises a fat.

30. The microparticle of claim 1, wherein the at least one emulsifier is a phospholipid.

31. The method of claim 14, wherein the at least one emulsifier is a phospholipid.

32. The microparticle of claim 1, wherein the agglomerating agent is a carbohydrate selected from the group consisting of glucose, fructose, galactose, sucrose, lactose, maltose, dextrose, glycogen, gums and combinations of these.

33. The microparticle of claim 1, wherein the agglomerating agent is a protein selected from the group consisting of animal proteins, milk proteins, zein proteins, vegetable proteins, protein isolates, protein hydrolyzates and combinations of these.

34. The method of claim 14, wherein the agglomerating agent is a carbohydrate selected from the group consisting of glucose, fructose, galactose, sucrose, lactose, maltose, dextrose, glycogen, gums and combinations of these.

35. The method of claim 14, wherein the agglomerating agent is a protein selected from the group consisting of animal proteins, milk proteins, zein proteins, vegetable proteins, protein isolates, protein hydrolyzates and combinations of these.

\* \* \* \* \*